United States Patent [19]

Morscher

[11] Patent Number: 4,769,041

[45] Date of Patent: Sep. 6, 1988

[54] HIP JOINT SOCKET

[75] Inventor: Erwin W. Morscher, Basel, Switzerland

[73] Assignees: Sulzer Brothers Limited, Winterthur; Protek AG, Berne, both of Switzerland

[21] Appl. No.: 879,283

[22] Filed: Jun. 27, 1986

[30] Foreign Application Priority Data

Jul. 15, 1985 [CH] Switzerland .................. 3063/85

[51] Int. Cl.$^4$ ............................................. A61F 2/34
[52] U.S. Cl. ...................................... 623/22; 623/20; 623/18
[58] Field of Search ............... 623/16, 17, 18, 19, 623/20, 21, 22, 23; 411/179, 180, 82

[56] References Cited

U.S. PATENT DOCUMENTS

| 3,125,146 | 3/1964 | Rosan | 411/180 |
|---|---|---|---|
| 3,128,813 | 4/1964 | Davis et al. | 411/180 |
| 3,133,579 | 5/1964 | Brum et al. | 411/180 |
| 3,461,936 | 8/1969 | Rosan, Sr. et al. | 411/180 |
| 3,840,904 | 10/1974 | Tronzo | 623/22 |
| 4,430,034 | 2/1984 | Fujikawa | 411/179 |
| 4,479,271 | 10/1984 | Boresky et al. | 623/20 |
| 4,563,778 | 1/1986 | Roche et al. | 623/16 |
| 4,566,138 | 1/1986 | Lewis et al. | 623/18 |

FOREIGN PATENT DOCUMENTS

| 0137664 | 4/1985 | European Pat. Off. | 623/22 |
|---|---|---|---|
| 3130732 | 5/1983 | Fed. Rep. of Germany | 623/22 |
| 3205526 | 9/1983 | Fed. Rep. of Germany | 623/22 |
| 3228113 | 2/1984 | Fed. Rep. of Germany | 623/22 |
| 2059267 | 4/1981 | United Kingdom | 623/16 |

*Primary Examiner*—Richard J. Apley
*Assistant Examiner*—David Isabella
*Attorney, Agent, or Firm*—Kenyon & Kenyon

[57] ABSTRACT

The hip joint socket has a plastic socket body which is covered on the outer surface with a multi-layer grid and which is provided with a plurality of peg-like projections of metal which are welded into the plastic socket body. The use of the metal projections and the metal grid prevent direct contact between the pelvic bone and plastic socket body in order to avoid disintegration of the plastic body by body fluids. The welding in of the projections provides a cost effective and small labor-intensive fixation of the projections in the socket body while ensuring firm and secure anchoring.

16 Claims, 1 Drawing Sheet

HIP JOINT SOCKET

This invention relates to a hip joint socket. More particularly, this invention relates to a hip joint socket for cement-free anchoring in a pelvic bone.

Heretofore, various types of hip joint sockets have been known for cement-free anchoring in a pelvic bone. In some cases, the hip joint sockets have been made of a plastic, such as polyethylene. However, in these cases, it has been found that over long periods of time, the plastic becomes attacked by body fluids and may disintegrate. For this reason, a procedure has been adopted whereby a plastic hip joint socket is embedded in a ring or a bowl of metal or ceramic, which, in turn, is firmly joined to the bone by accretion and/or ingrowth of tissue, for example as described in U.S. Pat. No. 3,874,297 and U.S. Pat. No. 3,840,904. However, this solution to the described problem has the disadvantage that the elasticity of the implant relative to the bone is lost.

A plurality of hip joint socket constructions are also known wherein peg-like projections protrude from the socket surface toward the bone for pressing into respective bores in the pelvis for anchoring of the socket in the pelvis. These projections are usually a component part of the socket and are intergrated into the socket body so that, in the case of sockets made of plastic, the projections also consist of plastic. Such constructions are shown in Swiss Pat. No. 644,511, U.S. Pat. No. 4,450,592 and German Pat. No. 3341724. However, where the projections are made of plastic, the problem of attack by the body fluids and disintegration exists. If made of metal, the elasticity of the implant relative to the bone is lost.

Accordingly, it is an object of the invention to provide a hip joint socket where direct contacts between bone and plastic are eliminated to the extent possible without unduly impairing the elasticity of a plastic hip joint socket body.

It is another object of the invention to provide a hip joint socket which utilizes a plastic body for elasticity purposes while preventing contact between the plastic body and the pelvic bone.

It is another object of the invention to provide a hip joint socket with good sliding properties and which can be firmly anchored in place.

Briefly, the invention provides a hip joint socket for cement-free anchoring in a pelvic bone which is comprised of a plastic body having a spherical outer surface, a multilayer metal grid secured to the surface of the plastic body for contacting a pelvic bone and a plurality of peg-like metal projections secured to the plastic body and extending outwardly of the grid for penetration into a pelvic bone in order to anchor the plastic body thereto.

The plastic body may be formed in a conventional manner with a conventional shape.

The multi-layer metal grid may be formed of a metal selected from the group consisting of titanium and titanium alloy with each layer formed as a wire mesh. The metal grid has little effect on the elasticity of the implant as the cross-sections of the wires or ridges can always be selected so that they do not unduly stiffen the implant. The provision of the metal grid in the plastic body at least drastically reduces or even practically eliminates contacts between the plastic body and the pelvic bone.

The peg-like projections which may also be made of titanium or a titanium alloy can best be secured to the plastic socket body by friction welding. Advantageously, the projections are formed as hollow cylindrical sleeves.

In order to improve the penetration of the hollow sleeves into the pelvic bone, each sleeve has a sharp peripheral edge at an outer end, formed, for example by a trumpet-like enlargement at the end of the bore of the sleeve. This shape also provides for a growth-promoting compaction of the bone substance which is displaced during penetration of the sleeve into the bone.

In order to limit the depth of penetration of the projections into the plastic of the socket body, each projection is appropriately enlarged in a base region in order to form a bearing plate while a hollow anchoring cylinder extends from the plate into the socket body. Loosening of the projections in the plastic body can be prevented by providing the bearing plate and/or the anchoring cylinder with groove-like depressions, for example, in the form of troughs and/or grooves and/or by providing the generated surface of the anchoring cylinder with peripherally disposed bores. The depressions in the bearing surface of the bearing plate and/or bores in the anchoring cylinder impede a rotation of the projection as well as movements due to shear forces while the ribs remaining between the depressions, possibly together with the bores in the anchoring cylinder, increase the resistance to movements in the axial direction of the projection.

The plastic of the plastic body is preferably one of the polyethylene modifications which is known and widely used in implant technology. The attachment of the metal grid on the outer surface of the plastic body is achieved in a simple manner by pressing the grid into the plastic softened by elevated temperature and under an elevated pressure. The temperature rise in the plastic body is limited to temperatures below the crystallite melting temperature (135° C. to 140° C.). The required pressure depends on the structure of the grid and on the selected temperature. For example, the pressure may be up to 4 kp per square millimeter.

In order to promote ingrowth and accretion of tissue, the grid may consist of more than two layers with the "pore size" of the grid openings increasing outwardly from layer to layer.

These and other objects and advantages of the invention will become more apparent from the following detailed description taken in conjunction with the accompany drawings wherein.

Figure 1:
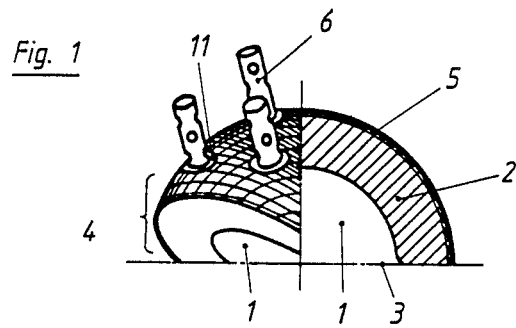
FIG. 1 illustrates a sectional view cut in half of a hip joint socket constructed in accordance with the invention.

Referring to FIG. 1, the hip joint socket is intended for cement-free anchoring in a pelvic bone. To this end, the hip joint socket has a plastic body 2 of substantially hemispherical shape so as to provide a spherical outer surface. As indicated, a socket bowl 1 for receiving an articular head (not shown) of a femur head prosthesis is fitted in known manner into the socket body 2. In order to enlarge the range of mobility of the femur head prosthesis, the socket body 2 is cut off obliquely in the region of the equator 3 on one side so that to make a "full" hemisphere, an orange wedge type piece 4 is required.

The hip joint socket also includes a multi-layer metal grid 5 which is secured to the outer surface of the plastic body for contacting a pelvic bone. In this regard, one layer of the metal grid is pressed into the plastic surface for anchoring purposes. As indicated in FIG. 3, each layer of the metal grid 5 may be formed of wire mesh.

The hip joint socket also has a plurality of peg-like metal projections 6 secured to the plastic body 2 and extending outwardly of the grid 5 for penetration into a pelvic bone in order to anchor the socket body 2 thereto. As indicated in FIG. 1 three projections 6 extend essentially radially of the outer surface of the socket body 2 while being disposed in a triangular array within the sector containing the bevel. As such, the three projections 6 point essentially in the direction of the main load of the socket.

Figure 3:
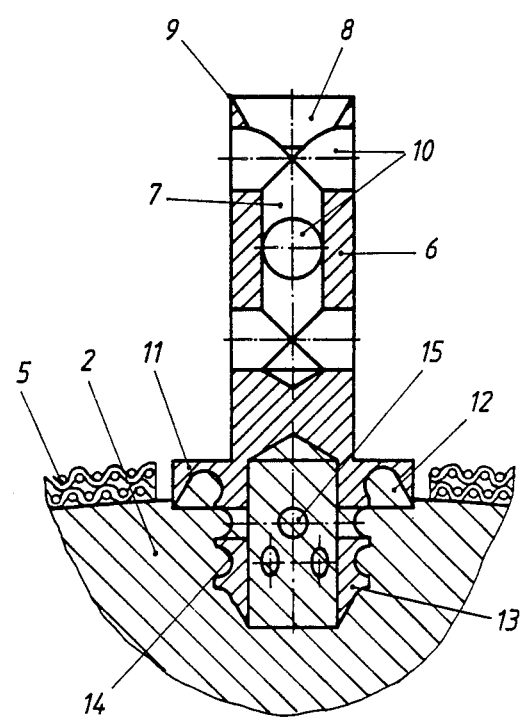
FIG. 3 illustrates an enlarged longitudinal sectional view of the manner of connecting a peg-like projection to the socket body in accordance with the invention.

Referring to FIG. 3, each projection 6 is in the form of a hollow cylindrical metal sleeve. Further, the sleeve has an internal bore 7 which terminates in a trumpet-like enlargement at the free end in order to define a sharp peripheral edge 9. This edge 9 serves as a "cutting edge" when the sleeve 6 is driven into the pelvic bone. The trumpet-like enlargement 8 facilitates the "flowing-in" of the then displaced bone into the bore 7 and causes a compaction of this bone tissue. In addition, the sleeve is provided with a plurality of peripherally disposed bores 10 into which tissue may grow.

Each projection also includes a bearing plate 11 at a base region of the sleeve in order to increase the support of the sleeve on the surface of a socket body 2 against forces acting in the direction of the sleeve axis. As shown, a plurality of trough-like depressions or grooves 12 are formed on the underside of the bearing surface of the plate 11 in order to increase resistance to rotational forces or to shearing forces acting along the surface of the socket body 2.

Each projection also has a hollow anchoring cylinder 13 which extends from the bearing plate 11 to penetrate into the socket body 2. This cylinder is also provided with a plurality of groove-like depressions 14 on the outside as well as a plurality of peripherally disposed bores 15.

Figure 2:
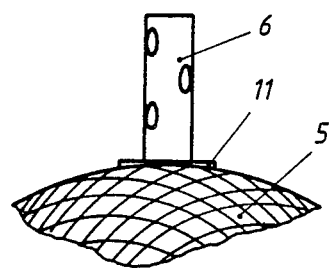
FIG. 2 illustrates a detailed view of the outer surface of the hip joint socket of FIG. 1 with a peg-like projection thereon.

As indicated in FIG. 3, the sleeve 6 is not connected with the grid 5 but has a clearance therefrom in the region of the bearing plate 11. Further, as indicated in FIGS. 2 and 3, the bearing plate 11 projects slightly above the thickness of the metal grid 5.

The mounting of the sleeve 6 in the socket body 2 occurs by friction welding. To this end, during welding, the plastic of the socket body 2 undergoes so strong a "softening" that the plastic permits penetration of the anchoring cylinder 13 while completely filling the cylinder as well as the bores 15 as indicated in FIG. 3. The main function of the anchoring cylinder 15 is to fix the sleeve 6 in the socket body 2 against tilting loads. The bores 15 and the depressions 14 increase the protection against rotational and tensile stresses.

During friction welding, the plastic of the socket body 2 also penetrates into the depressions 12 on the underside of the bearing plate 11 so as to further fix the sleeve 6 against rotation about the longitudinal axis thereof. As indicated in FIG. 3, the bearing plate 11 also penetrates somewhat into the socket body 2.

The metal grid 5 and the projection 6 may be formed of one of the metals known to be especially tissue-friendly, such as titanium, tantalum, niobium, zirconium or alloys with these metals as base materials. The grid 5 and projection 6 thus form a tissue-friendly surface structure into which bone tissue may grow in the course of time so that the hip joint socket is firmly anchored in the bone without bone cement.

Advantageously, the mesh width of at least one of the internal layers of the metal grid 5 can be made so narrow that tissue will grow in but not through the mesh. In this case, the grid brings about a complete shielding and separation between the pelvic bone and the plastic socket body 2.

The invention thus provides a hip joint socket in which disintegration of plastic due to attack by body fluids is substantially reduced if not eliminated.

Further, the invention provides a hip joint socket which can be firmly anchored in a cement-free manner in a pelvic bone while being inherently elastic relative to the pelvic bone.

The invention further provides a relatively simple and cost-effective technique for fabricating the hip joint socket of composite materials.

What is claimed is:

1. A hip joint socket for cement-free anchoring in a pelvic bone comprising
    a plastic body having a spherical outer surface;
    a metal grid disposed in said outer surface of said plastic body for contacting the pelvic bone, said grid including at least two layers of metal material; and
    at least one peg-like metal projection welded to and penetrating into said spherical outer surface of said plastic body inwardly beyond said metal grid, said projection extending outwardly of said surface and said grid for disposition in the pelvic bone.

2. A hip joint socket as set forth in claim 1 wherein said projection is a hollow cylindrical sleeve.

3. A hip joint socket as set forth in claim 2 wherein said sleeve has a bore with a trumpet-like enlargement atone end to define a sharp peripheral edge.

4. A hip joint socket as set forth in claim 1 wherein said projection includes a bearing plate at a base region welded to said plastic body and a hollow anchoring cylinder penetrating into said plastic body.

5. A hip joint socket as set forth in claim 4 wherein said cylinder includes a plurality of peripherally disposed bores.

6. A hip joint socket as set forth in claim 4 wherein at least one of said bearing plate and said cylinder has a plurality of groove-like depressions therein.

7. A hip joint socket as set forth in claim 1 wherein said projection is friction welded to said plastic body.

8. A hip joint socket as set forth in claim 1 wherein each of said grid and said projection is formed of a metal selected from the the group consisting of titanium and titanium alloy.

9. A hip joint socket for cement-free anchoring in a pelvic bone comprising
    a plastic body having a spherical outer surface;
    a multi-layer metal grid secured to said surface of said plastic body for contacting a pelvic bone; and
    a plurality of peg-like metal projections secured to said plastic body and extending outwardly of said grid for penetration into a pelvic bone to anchor said body thereto.

10. A hip joint socket as set forth in claim 9 wherein said projections are disposed in a triangular array.

11. A hip joint socket as set forth in claim 9 wherein each projection is a hollow cylindrical sleeve.

12. A hip joint socket as set forth in claim 11 wherein each sleeve has a sharp peripheral edge at an outer end.

13. A hip joint socket as set forth in claim 11 wherein each sleeve has periperally disposed bores for ingrowth of tissue.

14. A hip joint socket as set forth in claim 11 wherein each said projection includes a bearing plate at a base region welded to said plastic body and a hollow anchoring cylinder penetrating into said socket body.

15. A hip joint socket as set forth in claim 14 wherein each cylinder includes a plurality of peripherally disposed bores.

16. A hip joint socket as set forth in claim 14 wherein at least one of said bearing plate and said cylinder has a plurality of groove-like depressions therein.

* * * * *